(12) United States Patent
Gold et al.

(10) Patent No.: US 8,796,491 B2
(45) Date of Patent: Aug. 5, 2014

(54) PROCESS FOR MANUFACTURING ADAMANTANE DERIVATIVES WITH HIGH YIELD

(75) Inventors: Markus-Rene Gold, Karlstadt (DE); Herbert Koller, Vienna (AT); Michael Pyerin, Brunn Am Gebirge (AT)

(73) Assignee: Merz Pharma GmbH & Co. KGaA, Frankfurt am Main (DE)

( * ) Notice: Subject to any disclaimer, the term of this patent is extended or adjusted under 35 U.S.C. 154(b) by 356 days.

(21) Appl. No.: 12/737,716

(22) PCT Filed: Aug. 7, 2009

(86) PCT No.: PCT/EP2009/005751
§ 371 (c)(1),
(2), (4) Date: Apr. 25, 2011

(87) PCT Pub. No.: WO2010/015415
PCT Pub. Date: Feb. 11, 2010

(65) Prior Publication Data
US 2011/0263900 A1    Oct. 27, 2011

Related U.S. Application Data

(60) Provisional application No. 61/188,415, filed on Aug. 8, 2008.

(30) Foreign Application Priority Data

Aug. 8, 2008  (EP) .................................... 08014215

(51) Int. Cl.
*C07C 209/62*    (2006.01)
*C07C 231/10*    (2006.01)
(52) U.S. Cl.
USPC ......................................... 564/459; 564/217

(58) Field of Classification Search
USPC .................................................. 564/217, 459
See application file for complete search history.

(56) References Cited

U.S. PATENT DOCUMENTS 7,405,324 B2 *   7/2008   Vigano' et al. ................ 564/217
2008/0033054 A1 *  2/2008   Merli et al. ................... 514/662

FOREIGN PATENT DOCUMENTS

| LV | 13186 | 11/2004 |
| WO | 2006/122238 | 11/2006 |
| WO | 2008/062472 | 5/2008 |

OTHER PUBLICATIONS

European Search Report for EP08014215 dated Jan. 20, 2009.
Database WPI Week 100782, Thomson Scientific, London, GB, Nov. 10, 2007, XP002510980.
International Search Report for PCT/EP2009/005751 of Sep. 16, 2009.
Kisilenko.A.A., et al., "Bromine Complexes of 1-Bromoadamantanes" Journal of General Chemistry USSR, vol. 55, No. 12, p. 2370-2372, May 20, 1988.

* cited by examiner

*Primary Examiner* — Shailendra Kumar
(74) *Attorney, Agent, or Firm* — Hueschen and Sage

(57) ABSTRACT

The present invention pertains to process for the amidation of a substituted 1-bromo-adamantane comprising a step (0) of reacting a substituted adamantane with an excess of bromine to obtain a 1-bromo-adamantane and a step (i) of reacting said substituted 1-bromo-adamantane with an amide, wherein the substituted 1-bromo-adamantane is used in the form of a mixture comprising bromine as obtained in step (0), wherein in step (0) a bromine: substituted adamantane molar ratio of from [2.5:1] to less than [5:1] is employed.

13 Claims, No Drawings

PROCESS FOR MANUFACTURING ADAMANTANE DERIVATIVES WITH HIGH YIELD

This application is a 371 of PCTiEP2009i005751, filed Aug. 7, 2009, which claims benefit of 61/188,415, filed Aug. 8, 2008.

FIELD OF THE INVENTION

The present invention pertains to a process for manufacturing adamantane derivatives or pharmaceutical salts thereof with a yield of about 90%. In one embodiment of the present invention said process comprises a step of amidation, wherein substituted 1-bromo-adamantane, e.g. 1-bromo-3,5-dimethyladamantane, is reacted with an amide wherein the substituted 1-bromo-adamantane, e.g. 1-bromo-3,5-dimethyladamantane is used in the form of a mixture comprising bromine.

BACKGROUND OF THE INVENTION

Memantine (1-amino-3,5-dimethyl adamantane), its therapeutic use and methods for its preparation are known in the art. For a summary of the prior art in this respect reference is made to U.S. provisional application 61/062,602 and EP 08001545.6.

International Publication No. WO 2006/122238 discloses processes for preparing memantine or an acid addition salt of memantine, which involve either reaction of 1-bromo-3,5-dimethyladamantane with formamide to form N-formyl-1-amino-3,5-dimethyladamantane or reaction of 1-hydroxy-3,5-dimethyladamantane with a hydrogen halide to obtain 1-halo-3,5-dimethyl adamantane which is then reacted with formamide to yield N-formyl-1-amino-3,5-dimethyladamantane. The N-formyl-1-amino-3,5-dimethyladamantane intermediate is deformylated under acidic conditions to yield memantine hydrochloride. Excess of bromine is distilled off from the reaction mass, after the reaction is completed. The reactions disclosed therein are summarized in the following scheme 1:

Scheme 1

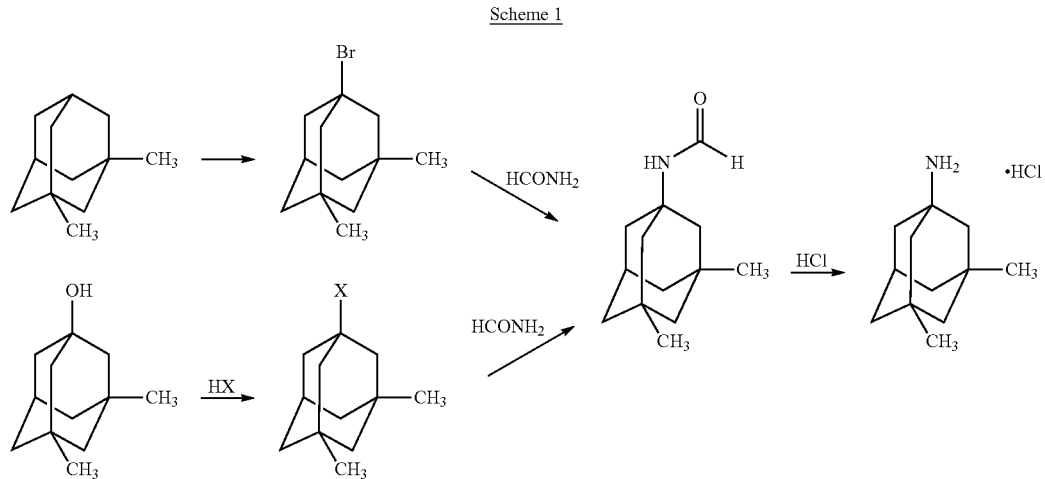

LV 1318613 B relates to a method of preparation of 1-amino-3,5-dimethyladamantane hydrochloride (memantine HCl) wherein 1,3-dimethyladamantane is reacted with nitric acid followed by addition of urea and heating of the reaction mixture. Nitric acid is added at 10-30° C. to the pre-formed emulsion of the hydrocarbon in acetic acid and subsequently, 30-55% of aqueous urea solution is added in the molar ratio 1,3-dimethyladamantane-acetic acid-urea 1:3-4:9-12:2.5-5-0 accordingly.

Kisilenko et al. ("*Bromine complexes of* 1-*bromoadamantanes*", Translation from Zhurnal Obshchei Khimii, vol. 57, No. 12, pg. 2659-2662, Plenum publishing corporation, pages 2370-2372, 1988) have shown that 1-bromoadamantanes form fairly stable complexes with bromine.

The Russian patent application RU 2 309 940 discloses a method for the preparation of 3,5-dimethyladamantyl-1-amine or its salts. The method includes a stage of bromination of 1,3-dimethyladamantane with liquid bromine while boiling. Bromination is carried out with a molar ratio of 1,3-dimethyladamantane to bromine of 1 to 2 to 8, or 1 to 3 to 6, and the bromine is separated off by distillation. When using the claimed method, the yield of the target product is 63 to 75%. DIKTAT MR WO 2008/062472 also relates to a process for preparing memantine or an acid addition salt of memantine comprising the reaction of 1-bromo-3,5-dimethyladamantane with formamide to form 1-N-formyl-3,5-dimethyl adamantane.

OBJECTS OF THE INVENTION

In view of the prior art, it was an object of the present invention to provide an advantageous process for preparing adamantane derivatives, e.g. memantine, or pharmaceutically acceptable salts thereof as well as intermediate products within the synthetic route for preparing adamantane derivatives starting from substituted adamantane.

The present invention pertains to a process for manufacturing adamantane derivatives or pharmaceutical acceptable salts thereof that avoids the step of distillation of excess of halogens and hence enables a one-step process. Moreover, the present invention overcomes the use of high temperatures during the amidation step, which enables a safe and environmental-friendly procedure. Particularly, the process disclosed herein is used to produce the desired product in higher yield than the prior art processes.

SUMMARY OF THE INVENTION

These and other objects are solved by a process comprises the amidation of a substituted 1-bromo-adamantane, e.g. 1-bromo-3,5-dimethyladamantane comprising a step (i) of reacting said substituted 1-bromo-adamantane, e.g. 1-bromo-3,5-dimethyladamantane, with an amide, wherein the substituted 1-bromo-adamantane, e.g. 1-bromo-3,5-dimethyladamantane is used in the form of a mixture comprising bromine.

In one embodiment the method of the present invention comprises a step (0) wherein an excess of bromine is reacted with a substituted adamantane, e.g. 1,3-dimethyladamantane resulting in a mixture of a substituted 1-bromo-adamantane, e.g. 1-bromo-3,5-dimethyladamantane and bromine.

In particular the invention relates to a process for the amidation of a substituted 1-bromo-adamantane comprising a step (0) of reacting a substituted adamantane with an excess of bromine to obtain a substituted 1-bromo-adamantane and a step (i) of reacting said substituted 1-bromo-adamantane with an amide, wherein the substituted 1-bromo-adamantane is used in the form of a mixture comprising bromine as obtained in step (0), wherein in step (0) a bromine:substituted adamantane molar ratio of from [2.5:1] to less than [5:1] is employed.

In one embodiment of the present invention the amidation product of step (i) is further processed in a step (ii) to a 1-aminoadamantane derivative or a pharmaceutically acceptable salt thereof.

In a further embodiment a bromine:substituted adamantane molar ratio from [2.8:1] to [3.5:1] is employed in step (0).

In one embodiment of the instant invention in step (0) the bromine:substituted adamantine molar ratio is [3:1].

In one embodiment the reaction temperature in step (0) is between 50 to 100° C.

The substituted 1-bromo-adamantane in said mixture of step (0) is present as a complex with bromine.

In one embodiment the substituted 1-bromo-adamantane is 1-bromo-3,5-dimethyladamantane or 1-bromo-3,5-diphenyladamantane.

In one embodiment the amide in step (i) is either acetamide or formamide.

In one embodiment the molar ratio between the substituted adamantane and formamide ranges from [1:3] to [1:10].

In one embodiment the substituted 1-bromo-adamantane and bromine are transferred to the formamide solution over a time period of 4 hours at a temperature ranging from 65° C. to 85° C. under constant agitation at 90 rpm to 100 rpm.

In one embodiment step (ii) comprises acid hydrolysis of the amidation product of step (i) by employing an organic acid or an inorganic acid or a mixture of two or more organic acids, or a mixture of two or more inorganic acids or a mixture of at least one organic acid and at least one inorganic acid.

In one embodiment the organic acid is selected from the group of para-toluenesulphonic acid, methanesulfonic acid, para-bromophenylsulphonic acid, carbonic acid, succinic acid, benzoic acid, maleic acid, tartaric acid, fumaric acid, methylsulfonic acid, formic acid, citric acid, acetic acid, oxalic acid and mixtures thereof and wherein the inorganic acid is selected from the group of hydrochloric acid, nitric acid, hydrobromic acid, sulfuric acid, phosphoric acid, nitric acid, hydroiodic acid and mixtures thereof.

In one embodiment the 1-aminoadamanatane derivative is selected from the group of memantine, amantadine, 1-Amino-methyladamantane, 1-Amino-3,5,7-trimethyladamantane, 1-Amino-3-ethyl-5-methyladamantane and 1-Amino-3-phenyladamantane, 1-Amino-3,5-dimethyladamantane, 1-Amino-3-ethyladamantane, 1-Amino-3-isopropyladamantane, 1-Amino-3-n-butyladamantane, 1-Amino-3,5-diethyladamantane, 1-Amino-3,5-diisopropyladamantane, 1-Amino-3-methyl-5-ethyladamantane, 1-Amino-3-butyl-5-phenyladamantane, 1-Amino-3-pentyladamantane, 1-Amino-3-dipentyladamantane, 1-Amino-3-pentyl-5-hexyladamantane, 1-Amino-3-pentyl-5-cyclohexyladamantane, 1-Amino-3-methyl-5-propyladamantane, 1-Amino-3-methyl-5-butyladamantane, 1-Amino-3-methyl-5-pentyladamantane, 1-Amino-3-methyl-5-hexyladamantane, 1-Amino-3-methyl-5-cyclohexyladamantane, 1-Amino-3-methyl-5-phenyladamantane, 1-Amino-3-ethyl-5-propyladamantane, 1-Amino-3-ethyl-5-butyladamantane, 1-Amino-3-ethyl-5-pentyladamantane, 1-Amino-3,5-dicyclohexyladamantane, 1-Amino-3-cyclohexyl-5-phenyladamantane, 1-Amino-3,5-diphenyladamantane, 1-Amino-3,5,7-trimethyladamantane, 1-Amino-3,5-dimethyl-7-ethyladamantane, 1-Amino-3-ethyl-5-hexyladamantane, 1-Amino-3-ethyl-5-cyclohexyladamantane, 1-Amino-3-ethyl-5-phenyladarnantane, 1-Amino-3-propyl-5-butyladamantane, 1-Amino-3-propyl-5-pentyladamantane, 1-Amino-3-propyl-5-hexyladamantane, 1-Amino-3-propyl-5-cyclohexyladamantane, 1-Amino-3-propyl-5-phenyladamantane, 1-Amino-3-butyl-5-pentyladamantane, 1-Amino-3-butyl-5-hexyladamantane, 1-Amino-3-butyl-5-cyclohexyladamantane or a pharmaceutically acceptable salt thereof.

In one embodiment the pharmaceutically acceptable salt of 1-aminoadamantane derivative is selected from the group of hydrochloric, hydrobromic, methylsulfonic, perchloric, sulfuric, phosphoric, acetic, nitric, propionic, glycolic, lactic, pyruvic, malonic, succinic, fumaric, tartaric, citric, benzoic, carbonic, cinnamic, mandelic, methanesulfonic, ethanesulfonic, hydroxyethanesulfonic, benezenesulfonic, p-toluene sulfonic, cyclohecanesulfamic, salicyclic, p-aminosalicylic, 2-phenoxybenzoic, 2-acetoxybenzoic, hydrobromic, hydroiodic, mesylate, phosphate, sulfate.

DETAILED DESCRIPTION OF THE INVENTION

The reaction steps (0), (i) and (ii) are illustrated in the figure below:

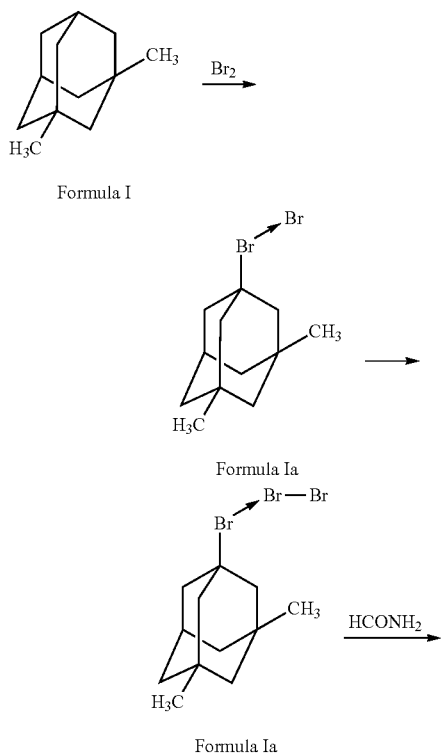

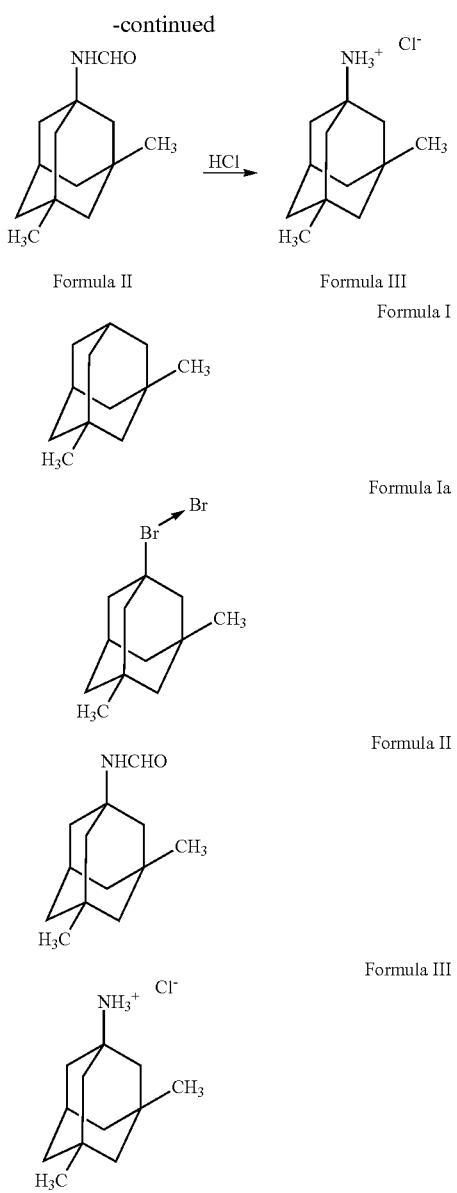

Formula II

Formula III

Formula I

Formula Ia

Formula II

Formula III

The above illustrated overall reaction can be carried out in a number of subsequent steps including the isolation of the product of formula II and/or formula III. Alternatively, it can be carried out without isolating any of the intermediate products. It is, however, essential within the present invention that after having conducted step (i), excess bromine is not separated off the obtained reaction mixture. One advantages of the subject process is an improved yield of the 1-bromo-alkyladamantane, e.g. 1-bromo-3,5-dimethyladamantane of up to 90 by weight.

In the following the individual steps as well as the overall reaction of the present invention are described in more detail.

The bromination according to step (0) is known in the prior art. It is possible within the present invention to prepare the substituted 1-bromo-adamantane, e.g. 1-bromo-3,5-dimethyladamantane according to any of the procedures according to the prior art.

Step (0) can be carried out in the presence of absence of an additional solvent. Such additional solvents include, but are not limited to, alcohols such as methanol, ethanol, propanol, and the like, ketones, such as acetone, ethyl methyl ketone, and the like, esters, such as ethyl acetate, propyl acetate, and the like, and mixtures thereof.

In one embodiment, the 1-bromo-alkyladamantane in said mixture resulting from step (0) is present as a complex with bromine, e.g. complex of bromine with 1-bromo-3,5-dimethyladamantane.

In one further embodiment, 1-bromo-phenyladamantane in said mixture resulting from step (0) is present as a complex with bromine, e.g. complex of bromine with 1-bromo-phenyladamantane.

In the step (0) the 1-bromo-alkyladamantane, e.g. 1-bromo-3,5-dimethyladamantane may be obtained by reacting bromine with substituted adamantane, e.g. 1,3-dimethyladamantane, at a molar ratio of from [2.8:1] to less than [5:1], e.g. [2.8:1] to [3.5:1].

In the step (0) the 1-bromo-alkyladamantane, e.g. 1-bromo-3,5-dimethyladamantane may be obtained by reacting bromine with substituted adamantane, e.g. 1,3-dimethyladamantane at a molar ratio of [2.8:1].

In the step (0) the 1-bromo-alkyladamantane, e.g. 1-bromo-3,5-dimethyladamantane may be obtained by reacting bromine with substituted adamantane, e.g. 1,3-dimethyladamantane at a molar ratio of [3:1].

The bromine may be added to substituted adamatane under an agitation speed of 50 to 100 rpm, e.g. at an agitation speed of about 90 rpm.

The reaction according to step (0) may be carried out under inert atmosphere, e.g. under nitrogen atmosphere.

Typically, the bromine is added to the substituted adamantane, usually in a slow manner with careful control of temperature of the reaction. In one further embodiment of the present invention, the reaction temperature in step (0) is between 50 to 100° C., e.g. about 80° C.

Within the scope of this invention the substituted adamantane as employed in step (0) may be, but is not limited to, alkyl-substituted adamantane, halosubstituted adamantane, phenyl-substituted adamantane, substituted phenyl-substituted adamantane, wherein phenyl may be substituted with different functional groups such as nitro groups, halogens such as bromine, iodine or chlorine, alkoxy groups such as ethoxy, methoxy or hydroxyl groups. Examples of substituted phenyl-substituted adamantanes are but not limited to 1-(3-phenyl-3-hydroxypropylamino)adamantane, 1-(3-phenyl-oxopropylamino)adamantane, 1-(3-phenyl-3-oxo-2-methyl-propylamino)adamantane. The alkyladamantanes may comprise 1 to 3 alkyl substituents, wherein each alkyl substituent has the same number or a different number of carbon atoms.

Examples for substituted adamantanes that may be reacted with an excess of bromine in step (0) are, but are not limited to, methyladamantane, ethyladamantane, methylethyladamantane, dimethyladamantane, triethyladamantane, trimethyladamantane. Moreover, examples for alkyladamantanes that may be reacted with an excess of bromine are, but not limited to, 1-methyladamantane, 2-methyladamantane, 1,2-dimethyladamantane, 1,3-dimethyladamantane and 1,4-dimethyladamantane, 1,2,4-trimethyladamantane, 1,2,5-trimethyladamantane, 1,3,4-trimethyladamantane, 1,3,5-trimethyladamantane, 1,3,6-trimethyladamantane, 1-ethyladamantane, 2-ethyladamantane, 1-ethyl-3-methyladamantane, 1-ethyl-4-methyladamantane, 1-ethyl-2,4-dimethyladamantane, 1-ethyl-3,5-dimethyladamantane, 1-ethyl-3,6-dimethyladamantane. Further examples of these starting alkyladamantanes that may be reacted with excess of bromine in step (0) are, but not limited to, 1-methyl-3-propyladamantane, 1,2-diisobutyladamantane, 1-ethyl-2-methyl-5-amyladamantane, 1-butyladamantane, 2-butyladamantane and such.

In another embodiment the method of the present invention comprises a step (0) wherein excess of bromine is reacted with 1,3,5-trimethyladamantane resulting in a mixture of 1-bromo-3,5,7-trimethyladamantane and bromine.

In step (i) an amide is added to the mixture obtained from step (0). Typically the temperature within step (i) ranges from 75 to 120° C. In one embodiment of the present invention the reaction temperature of the amidation step (i) does not exceed 120° C.

The amide used in step (i) may be selected among acetamide and substituted acetamides e.g. chloracetamide and formamide.

In one embodiment of the present invention the amide in step (i) is formamide, and the respective product is 1-formamido-alkyladamantane, e.g. 1-formamido-3,5-dimethyladamantane.

The molar ratio between substituted adamantane and the amide, e.g. the ratio between 1,3-dimethyladamantane and formamide is at least [1:3], e.g. 1:6.5.

In one embodiment of the present invention urea or an urea derivative is used in step (i) wherein 1-bromo-alkyladamantane is reacted with urea or an urea derivative. Examples of urea derivatives are, but not limited to, N,N-dimethylurea, N,N-diethylurea, N,N-di-n-propylurea, N,N-diisopropylurea, N,N-dibutylurea, N,N-dicyclohexylurea, thiourea and such.

In another embodiment of the present invention the molar relationship of 1-bromo-alkyladamantane to urea is [1:2].

Suitable solvents which can be used within step (i) include, but are not limited to alcohols such as methanol, ethanol, propanol, butanol, and the like; ketones such as acetone, ethyl methyl ketone, methyl isobutyl ketone, and the like; esters such as ethyl acetate, propyl acetate, and the like; and mixtures thereof. Step (i) may be also carried out without using any solvent, i.e. the amide itself may act as a solvent.

In one embodiment of the present invention the mixture of 1-bromo-alkyladamantane and bromine, e.g. 1-bromo-3,5-dimethyladamantane and bromine is transferred to the acetamide solution over a time period of 4 hours at about 75° C. under constant agitation at about 100 rpm. In another embodiment of the present invention this step is conducted in the reverse sequence, i.e. the acetamide solution is transferred to the mixture of 1-bromo-alkyladamantane and bromine over a time period of 4 hours at about 75° C. under constant agitation at about 100 rpm.

In one embodiment of the present invention the mixture of 1-bromo-alkyladamantane and bromine, e.g. 1-bromo-3,5-dimethyladamantane and bromine is transferred to the formamide solution over a time period of 4 hours at about 75° C. under constant agitation at about 100 rpm. In another embodiment of the present invention this step is conducted in the reverse sequence, i.e. the formamide solution is transferred to the mixture of 1-bromo-alkyladamantane and bromine over a time period of 4 hours at about 75° C. under constant agitation at about 100 rpm.

After completion of the amidation, the reaction mass may be quenched with a protic solvent. Said quenching is again known in the art. Protic solvents that may be used include, but are not limited to, water, alcohols, acetic or formic acid, or mixtures thereof. The addition of the protic solvent is typically carried out at relatively low temperatures of below 30° C.

In another embodiment of the present invention step (ii) comprises acid hydrolysis of the amidation product of step (i) by employing either organic acid or inorganic acid, or a mixture of two or more thereof. Acid hydrolysis according to the present invention is provided by adding either organic or inorganic acids (diluted or concentrated acid). Organic acids as used herein include, but are not limited to, para-toluenesulphonic acid, methanesulfonic acid, para-bromophenylsulphonic acid, carbonic acid, succinic acid, benzoic acid, maleic acid, tartaric acid, fumaric acid, methylsulfonic acid, formic acid, citric acid, acetic acid, oxalic acid or mixtures thereof. Inorganic acids as used herein are, but not limited to, hydrochloric acid, nitric acid, hydrobromic acid, sulfuric acid, phosphoric acid, nitric acid, hydroiodic acid.

In one further embodiment the inorganic acid is hydrochloric acid. Typically, the molar ratio between substituted adamantane and hydrochloric acid, e.g. 1,3-dimethyladamantane and hydrochloric acid is at least 1:2, in another embodiment 1:5.8. In principal the ratio adamantane derivative:acid can vary in a broad range up to a 10 to 100-fold molar excess of acid compared to the adamantane derivative.

Said step (ii) may again be carried out in the presence of a solvent, such as, but not limited to, alcohols, ketones, nitriles, DMSO, DMF, or mixtures thereof, optionally in combination with water in various proportions without limitation. Suitable temperatures within step (ii) are within about 0 to 150° C.

Specific embodiments of the adamanatane derivative obtained via step (ii) are, but not limited to, memantine, 1-Amino-methyladamantane, 1-Amino-3,5,7-trimethyladamantane, 1-Amino-3-ethyl-5-methyladamantane and amantadine, 1-Amino-3-phenyladamantane, 1-Amino-3,5-dimethyladamantane, 1-Amino-3-ethyladamantane, 1-Amino-3-isopropyladamantane, 1-Amino-3-n-butyladamantane, 1-Amino-3,5-diethyladamantane, 1-Amino-3,5-diisopropyladamantane, 1-Amino-3-methyl-5-ethyladamantane, 1-Amino-3-butyl-5-phenyladamantane, 1-Amino-3-pentyladamantane, 1-Amino-3-dipentyladamantane, 1-Amino-3-pentyl-5-hexyladamantane, 1-Amino-3-pentyl-5-cyclohexyladamantane, 1-Amino-3-methyl-5-propyladamantane, 1-Amino-3-methyl-5-butyladamantane, 1-Amino-3-methyl-5-pentyladamantane, 1-Amino-3-methyl-5-hexyladamantane, 1-Amino-3-methyl-5-cyclohexyladamantane, 1-Amino-3-methyl-5-phenyladamantane, 1-Amino-3-ethyl-5-propyladamantane, 1-Amino-3-ethyl-5-butyladamantane, 1-Amino-3-ethyl-5-pentyladamantane, 1-Amino-3,5-dicyclohexyladamantane, 1-Amino-3-cyclohexyl-5-phenyladamantane, 1-Amino-3,5-diphenyladamantane, 1-Amino-3,5,7-trimethyladamantane, 1-Amino-3,5-dimethyl-7-ethyladamantane, 1-Amino-3-ethyl-5-hexyladamantane, 1-Amino-3-ethyl-5-cyclohexyladamantane, 1-Amino-3-ethyl-5-phenyladamantane, 1-Amino-3-propyl-5-butyladamantane, 1-Amino-3-propyl-5-pentyladamantane, 1-Amino-3-propyl-5-hexyladamantane, 1-Amino-3-propyl-5-cyclohexyladamantane, 1-Amino-3-propyl-5-phenyladamantane, 1-Amino-3-butyl-5-pentyladamantane, 1-Amino-3-butyl-5-hexyladamantane, 1-Amino-3-butyl-5-cyclohexyladamantane.

Instead of these compounds themselves, also pharmaceutically acceptable salts thereof may be obtained by using methods known in the art. The pharmaceutically acceptable salts of the desired adamantane derivative include, but not limited to acid addition salts, such as those made with hydrochloric, methylsulfonic, perchloric, sulfuric, phosphoric, acetic, propionic, glycolic, lactic, pyruvic, malonic, succinic, fumaric, tartaric, citric, benzoic, carbonic, cinnamic, mandelic, methanesulfonic, ethanesulfonic, hydroxyethanesulfonic, benezenesulfonic, p-toluene sulfonic, cyclohecanesulfamic, salicyclic, p-aminosalicylic, 2-phenoxybenzoic, and 2-acetoxybenzoic acid. The nature of the salt is not particularly critical, provided that it is non-toxic and does not substantially interfere with the desired pharmacological activity. Specific salts to be prepared according to the present invention are memantine hydrochloride or memantine mesylate.

In the following a number of terms used in the above description of the invention are defined to improve the understanding of the subject matter of the same.

The term "about" as used herein is intended to reflect a variation of 10% of the value it is attached to.

The term "compound" as used herein refers to all substances comprising at least two elements bound to each other.

The term "mixture" as used herein is a combination of two or more molecules, atoms, ions or any combinations or complexes thereof, independent from the way they are combined. The term "mixture" as used herein might be a chemical or a physical mixture.

The term "pharmaceutical acceptable" as used herein refers to molecular structures, compounds or complexes that are physiologically tolerable and do not produce any unwanted reaction when administered to a mammal.

The term "salts" as used herein includes salts of free acids or free bases.

The term "complex" as used herein refers to a structure comprising a central molecule, atom, ion or combination thereof connected with chemical or physical bonds to surrounding atoms, molecules or ions. The central atom or molecule may be in ionized or in non-ionized form.

The term "alkyl" as used herein refers to straight and branched chain saturated aliphatic groups typically having from 1 to 20 carbon atoms, in another embodiment having from 1 to 6 carbon atoms, as well as cyclic saturated aliphatic groups typically having from 3 to 20 carbon atoms and in one further embodiment having from 3 to 6 carbon atoms. Examples of alkyl groups according to this invention are, but not limited to, methyl, ethyl, propyl, butyl, isopropyl, isobutyl, sec-butyl, t-butyl, cyclopropyl, cyclobutyl, cyclopentyl, cyclohexyl and the like.

The term "alkyl" as used herein refers also to substituted alkyls, which are alkyl groups as defined above, having 1 to 5 substituents. In one embodiment alkyl groups have 1 to 3 substituents. Said substituents are selected from the group consisting of alkoxy, substituted alkoxy, cycloalkyl, substituted cycloalkyl, cycloalkenyl, substituted cycloalkenyl, acyl, acylamino, acyloxy, amino, substituted amino, azido, cyano, halogen, hydroxyl, keto, thioketo, thiol, carboxyl, aryloxy, nitro, aryl and halogens.

The term "phenyl" as used herein refers to a benzene ring.

The term "substituted phenyl" as used herein refers to a phenyl group substituted with one or more groups independently selected from halogens, ($C_1$-$C_{10}$) alkyl, branched ($C_3$-$C_6$) alkyl, halo ($C_1$-$C_7$) alkyl, hydroxy ($C_1$-$C_7$) alkyl, ($C_1$-$C_7$) alkoxy, halo ($C_1$-$C_7$) alkoxy, phenoxy, phenyl, $NO_2$, OH, CN, ($C_1$-$C_4$) alkanoyl, benzoyl, ($C_1$-$C_4$) alkanoyloxy, ($C_1$-$C_4$) alkoxycarbonyl, phenoxycarbonyl, or benzoyloxy and such. Substituents may be same or different.

The terms "halo" and "halogen" are used synonymously, meaning a monovalent radical selected from the group of Chloro (Cl), Bromo (Br), Iodo (I) and Fluoro (F).

The invention is now described with reference to the following examples. These examples are provided for the purpose of illustration only and the invention should not be construed as being limited to these examples, but rather should be construed to encompass any and all variations which become evident as a result of the teaching provided herein. The following materials and methods are provided with respect to the subsequent examples but do not limit a multiplicity of materials and methodologies encompassed by the present invention.

EXAMPLES

Example 1

A clean enameled reactor is inerted by purging 3 times with nitrogen. Temperature in the reactor is adjusted to 20° C. 1.22 kmol of 1,3-dimethyladamantan is introduced into the reactor under nitrogen atmosphere. Consequently, 3.66 kmol of bromine is introduced into the reactor under constant agitation at 90 rpm. The reaction mass is heated up to 80° C. in approximately 8 hours under constant agitation at 90 rpm. The reaction mass is agitated for another 6 hours at 80° C.

A second reactor is prepared and the atmosphere in the reactor is inerted by purging the reactor 3 times with nitrogen. 7.9 kmol of formamide is introduced under nitrogen atmosphere at 22° C. into the reactor. Consequently, formamide is heated up to 75° C. under constant agitation at 100 rpm. The reaction mass in the first reactor is slowly, over a time period of 4 hours, transferred into the reactor containing formamide. The resulting mixture is agitated for 2 hours. After the preceding of 2 hours of agitation, the reactor is immediately cooled to 12° C. Methylene chloride is introduced to this reactor at 12° C. Immediately thereafter, bisulfite solution is prepared in a third reactor at 20° C. and consequently cooled down to 10° C. Slowly, over a time period of 2-3 hours, the bisulfite solution is transferred under constant agitation at 100 rpm into the second reactor containing the reaction mass. After 15 minutes two phases are formed; the brown upper phase containing the product and the aqueous layer phase containing the salts. The two phases are separated. Separately, a sodium bicarbonate solution is prepared and introduced into the brown organic phase. After 30 minutes, the mass is rinsed with Water for Injection. 7.06 kmol of hydrochloric acid is introduced to the resulting reaction mass and is heated to until reflux (T=98-108° C.). The resulting slurry is cooled immediately to 8° C. within 2.5 hours. The output is memantine HCl.

Example 2

The same procedure of example 1 is repeated with 1,3,5-trimethyladamantane resulting in 1-Amino-3,5,7-trimethyladamantane.

Example 3

The same procedure of example 1 is repeated with 1-methyl-3-propyladamantane resulting in 1-Amino-3-methyl-5-propyladamantan.

Example 4

The same procedure of example 1 is repeated with 1,3-diethyladamantan resulting in 1-Amino-3,5-diethyladamantan.

Example 5

The same procedure of example 1 is repeated with 1-propyl-5-cyclohhexyladamantan resulting in 1-Amino-3-propyl-5-cyclohhexyladamantan.

Example 6

The same procedure of example 1 is repeated with 1-phenyladamantane resulting in 1-amino-3-phenyl adamantane.

Example 7

The same procedure of example 1 is repeated with 1,3-diphenyladamantan resulting in 1-amino-3,5-diphenyladamantane.

Example 8

1.22 kmol of 1,3-dimethyladamantan is introduced into the reactor under nitrogen atmosphere. Consequently, 3.66 kmol of bromine is introduced into the reactor under constant agitation at 90 rpm. The reaction mass is heated up to 80° C. in approximately 8 hours under constant agitation at 90 rpm. The reaction mass is agitated for another 6 hours at 80° C.

A second reactor is prepared and 7.9 kmol of N,N-dimethylurea is introduced under nitrogen atmosphere into the reactor. Consequently, N,N-dimethylurea is heated up to 75° C. under constant agitation at 100 rpm. The reaction mass in the first reactor is slowly, transferred into the reactor containing N,N-dimethylurea. The resulting mixture is agitated for 2 hours, then the reactor is immediately cooled to 15° C. Methylene chloride is introduced to this reactor. Immediately thereafter, bisulfite solution is prepared in a third reactor at 20° C. and consequently cooled down to 10° C. Slowly, over a time period of 2-3 hours, the bisulfite solution is transferred under constant agitation at 100 rpm into the second reactor containing the reaction mass. After 15 minutes two phases are formed; the upper phase containing the product and the aqueous layer phase containing the salts. The two phases are separated. Separately, a sodium bicarbonate solution is prepared and introduced into the brown organic phase. After 30 minutes, the mass is rinsed with Water for Injection. 7.06 kmol of hydrochloric acid is introduced to the resulting reaction mass and is heated to until reflux (T=98-108° C.). The resulting slurry is cooled immediately to 8° C. within 2.5 hours. The output is memantine HCl.

The invention claimed is:

1. A process for the amidation of a substituted 1-bromo-adamantane comprising: step (0), wherein a substituted adamantane is reacted with an excess of bromine, wherein the reaction temperature in step (0) is between 50 to 100° C., to obtain a 1-bromo-adamantane and step (i), wherein the substituted 1-bromo-adamantane is reacted with an amide or urea and/or derivatives thereof to produce an amidation product, wherein the substituted 1-bromo-adamantane is used in the form of a mixture with bromine as obtained in step (0), and wherein, in step (0), a bromine: substituted adamantane molar ratio of from [2.8:1] to [3.5:1] is employed.

2. The process according to claim 1, further comprising step (ii), wherein the amidation product of step (i) is converted to a 1-aminoadamantane derivative or a pharmaceutically acceptable salt thereof.

3. The process according to claim 2, wherein the bromine: substituted adamantane molar ratio is [3:1].

4. The process according to claim 1, wherein the substituted 1-bromo-adamantane in the mixture is present as a complex with bromine.

5. The process according to claim 1, wherein the substituted 1-bromo-adamantane is 1-bromo-3,5-dimethyladamantane.

6. The process according to claim 1, wherein the substituted 1-bromo-adamantane is 1-bromo-3,5-diphenyladamantane.

7. The process according to claim 1, wherein the amide is acetamide or formamide.

8. The process according to claim 7, wherein a molar ratio between the substituted adamantane and formamide of from 1:3 to 1:10 is employed.

9. The process according to claim 7, wherein substituted 1-bromo-adamantine and bromine are transferred to the formamide solution over a time period of 4 hours at a temperature ranging from 65° C. to 85° C. under constant agitation at 90 rpm to 100 rpm.

10. The process according to claim 2, wherein step (ii) comprises acid hydrolysis of the amidation product of step (i) by employing an organic acid or an inorganic acid or a mixture of two or more organic acids, or a mixture of two or more inorganic acids or a mixture of at least one organic acid and at least one inorganic acid.

11. The process according to claim 10, wherein the organic acid is selected from the group of para-toluenesulphonic acid, methanesulfonic acid, para-bromophenylsulphonic acid, carbonic acid, succinic acid, benzoic acid, maleic acid, tartaric acid, fumaric acid, methylsufonic acid, formic acid, citric acid, acetic acid, oxalic acid and mixtures thereof and wherein the inorganic acid is selected from the group of hydrochloric acid, nitric acid, hydrobromic acid, sulfuric acid, phosphoric acid, nitric acid, hydroiodic acid and mixtures thereof.

12. The process according to claim 2, wherein the 1-aminoadamantane derivative is selected from the group of memantine, amantadine, 1-Amino-methyladamantane, 1-Amino-3,5,7-trimethylada-mantane, 1-Amino-3-ethyl-5-methyladamantane and 1-Amino-3-phenyladamantane, 1-Amino-3,5-dimethyladamantane, 1-Amino-3-ethyl-adamantane, 1-Amino-3-isopropyladamantane, 1-Amino-3-n-butyl-adamantane, 1-Amino-3,5-diethyladamantane, 1-Amino-3,5-diisopropyl-adamantane, 1-Amino-3-methyl-5-ethyladamantane, 1-Amino-3-butyl-5-phenyladamantane, 1-Amino-3-pentyladamantane, 1-Amino-3-dipentyl-adamantane, 1-Amino-3-pentyl-5-hexyladamantane, 1-Amino-3-pentyl-5-cyclohexyladamantane, 1-Amino-3-methyl-5-propyladamantane, 1-Amino-3-methly-5-butyladamantane, 1-Amino-3-methyl-5-pentylada-mantane, 1-Amino-3-methyl-5-hexyladamantane, 1-Am ino-3-methyl-5-cyclohexyladamantane, 1-Amino-3-methyl-5-phenyladamantane, 1Amino-3-ethyl-5-propyladamantane, 1-Amino-3-ethyl-5-butyladamantane, 1-Amino-3-ethyl-5-pentyladamantane, 1-Amino-3,5-dicyclohexylada-mantane, 1-Amino-3-cyclohexyl-5-phenyladamantane, 1-Amino-3,5-di-phenylada-mantane, 1-Amino-3,5,7-trimethyladamantane, 1-Amino-3,5-dimethyl-7-ethyladamantane, 1-Amino-3-ethyl-5-hexyladamantane, 1-Amino-3-ethyl-5-cyclohexyladamantane, 1-Amino-3-ethyl-5-phenyl-adamantane, 1-Amino-3-propyl-5-butyladamantane, 1-Amino-3-propyl-5-pentyladamantane, 1-Amino-3-propyl-5-hexyladamantane, 1-Amino-3-propyl-5-cyclohhexylada-mantane, 1-Amino-3-propyl-5-phenyladamantane, 1-Amino-3-butyl-5-pentyladamantane, 1-Amino-3-butyl-5-hexyladamantane, 1-Amino-3-butyl-5-cyclohexyladamantane or a pharmaceutically acceptable salt thereof.

13. The process according to claim 1, wherein the pharmaceutically acceptable salt of 1-aminoadamantane derivative is selected from the group of hydrochloric, hydrobromic methylsufonic, perchloric, sulfuric, phosphoric, acetic, nitric, propionic, glycolic, lactic, pyruvic, malonic, succinic, fumaric, tartaric, citric, benzoic, carbonic, cinnamic, mandelic, methanesulfonic, ethanesulfonic, hydroxyethanesulfonic, benezenesulfonic, p-toluene sulfonic, cyclohecanesulfamic, salicyclic, p-aminosalicylic, 2-phenoxybenzoic, 2-acetoxybenzoic, hydrobromic, hydroiodic, mesylate, phosphate, sulfate.

\* \* \* \* \*